United States Patent [19]

Michaud

[11] 4,271,120
[45] Jun. 2, 1981

[54] CORROSIVE FLUID DETECTOR

[75] Inventor: Louis M. Michaud, Port Elgin, Canada

[73] Assignee: Nova Scotia Research Foundation Corporation, Nova Scotia, Canada

[21] Appl. No.: 109,930

[22] Filed: Jan. 7, 1980

[30] Foreign Application Priority Data

Jan. 11, 1979 [CA] Canada ............................ 319452

[51] Int. Cl.³ ............................................. G01N 17/00
[52] U.S. Cl. ................................... 422/53; 23/230 C
[58] Field of Search ..................... 422/53; 23/230 C; 116/208, 278

[56] References Cited

U.S. PATENT DOCUMENTS 3,621,810  11/1971  Zuck, Jr. ................................ 422/53

FOREIGN PATENT DOCUMENTS 523622  4/1956  Canada .
757407  4/1967  Canada .
910733  9/1972  Canada .

*Primary Examiner*—Ronald Serwin
*Attorney, Agent, or Firm*—Roylance, Abrams, Berdo & Farley

[57] ABSTRACT

A device for detecting and indicating the presence of corrosive fluids in a specified volume, as in the insulating blanket surrounding the pipes in a heavy water plant, is disclosed. The device includes a housing containing a primary indicator such as a bobbin with a long, brightly colored ribbon wrapped therearound, and a secondary indicator. A compression spring abuts the secondary indicator and is held in compression by a corrodable link anchored at one end to the housing and at the other end to the secondary indicator. The link is exposed to the volume being monitored and if there is a corrosive fluid present the fluid will corrode the link until it breaks. The spring force is released to act on the secondary indicator to project the primary indicator from the housing. The ribbon unwinds from the bobbin to provide a visual indication of the presence of the corrosive fluid. The device of the present invention is reliable and inexpensive and can be readily produced in various and adjustable sizes to accommodate many applications.

17 Claims, 4 Drawing Figures

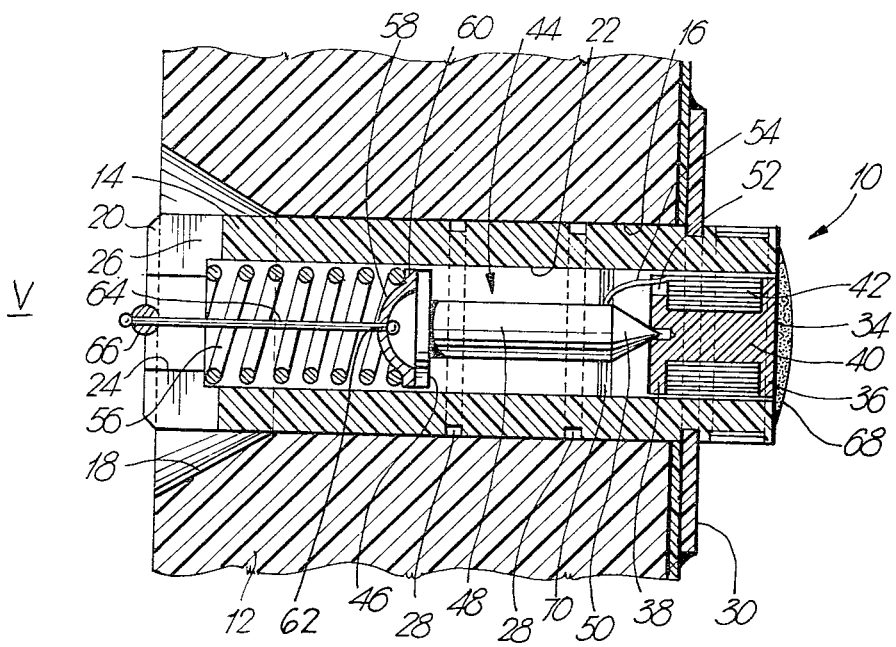
Fig-1
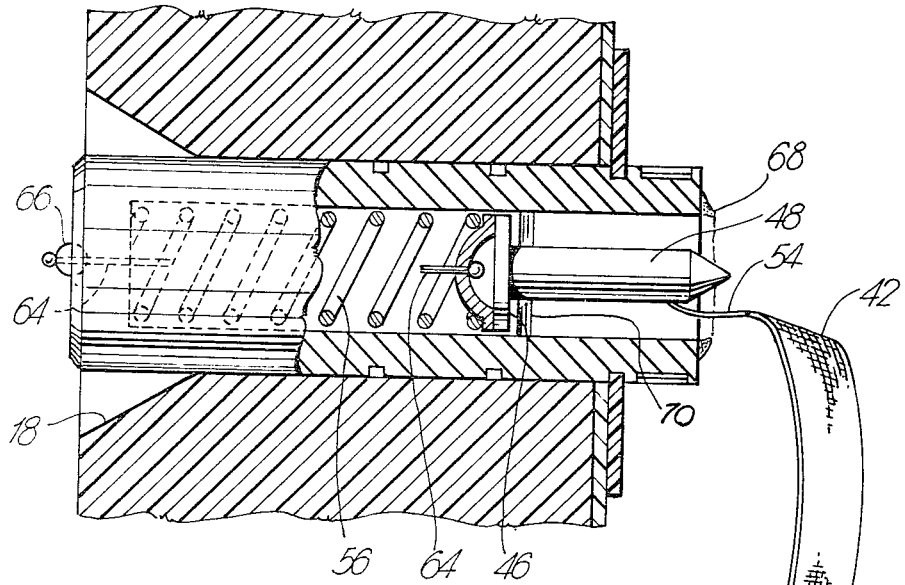
Fig-2
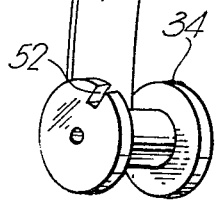

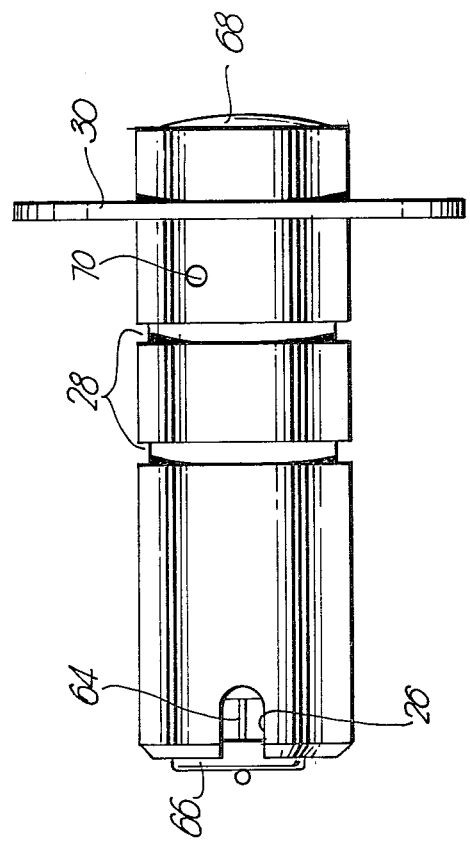
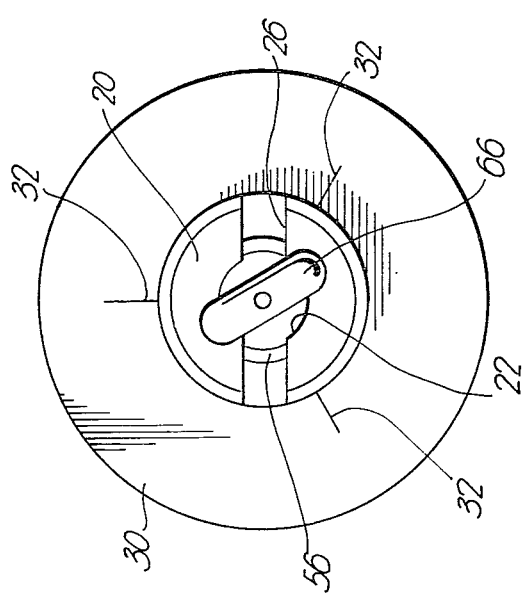

CORROSIVE FLUID DETECTOR

The present invention relates broadly to fluid detectors and in general to a detector for corrosive fluids.

BACKGROUND OF THE INVENTION

In the manufacture of heavy water, i.e. deuterium, the heavy water is extracted from natural water through an exchange with hydrogen sulfide. In a large production facility for the manufacture of heavy water a tremendous collection of pipes and their necessary flanged connections is involved. In fact, in a typical heavy water plant there are over 10,000 flanged connections. In the Canadian environment, two inches or so of insulation is placed over all the piping and their flanges to prevent heat loss. In the event of a leak at a flanged connection, hydrogen sulfide and water will be released to the interior of the insulation where they may combine with oxygen in the air to form both sulfuric and sulfurous acids. Such a combination is highly corrosive and can attack the tie bolts holding the flanges together to the point where an explosive separation could occur, releasing large quantities of hydrogen sulfide. This is of course of great concern to the heavy water industry. Needless to say there are other industries which generate corrosive gases or liquids, the leakage of which is detrimental to the safety of personnel and equipment. It therefore becomes necessary to be able to detect and indicate the presence of corrosive fluids as early as possible so that corrective measures, if required may be carried out.

DESCRIPTION OF THE PRIOR ART

There have been very few attempts in the past to develop detectors and indicators relative to corrosive fluids. Condition indicators using flags to visually indicate a specific condition are illustrated in Canadian Pat. Nos. 757,407 (O'Brien, issued Apr. 25, 1967) and 910,733 (Ranney et al., issued Sept. 26, 1972). Of perhaps greater interest is the fluid detector of Canadian Patent No. 523,622 (Shaw, issued Apr. 10, 1956) which shows a visual indicator which tells an observer when a baby's diaper is wet. A paper strip is held in tension by an elastic band and carries an indicator. When the strip becomes wet its tensile strength decreases due to a weakening of the interfibre bonds until the strip breaks. The elastic band, upon the breaking of the strip, brings the indicator into view. While of interest at the domestic level the teachings of this patent would not be applicable in the projected environments of industry.

SUMMARY OF THE INVENTION

The present invention aims to provide a simple, reliable device which may be readily inserted in the insulation wrapped around the pipes in a heavy water plant or in any wall defining a volume in which a corrosive fluid could be present. The present invention, if used in the heavy water situation, would be placed in the insulation jacket very near to the flange joint so that the release of hydrogen sulfide and the formation of corrosive acids will be detected early enough so that corrective measures may be taken.

Broadly speaking the present invention may be defined as a device for detecting and indicating the presence of a corrosive fluid, comprising a housing; primary indicating means in the housing; compression spring means in the housing adjacent the primary indicating means; and corrodable link means holding the spring means in compression; whereby when the link means is severed through corrosion thereof, the spring means acts on the primary indicating means to project said primary indicating means from said housing to an indicating condition.

BRIEF DESCRIPTION OF THE DRAWINGS

FIG. 1 is a vertical longitudinal section of the device of the present invention prior to activation.

FIG. 2 is a view similar to FIG. 1 showing the device of the present invention following activation.

FIG. 3 is an elevation of the assembled device of the present invention.

FIG. 4 is an end view of the assembled device.

DESCRIPTION OF THE PREFERRED EMBODIMENT

FIG. 3 shows the device of the present invention as it might be purchased by a consumer and FIG. 1 shows the device, in section, as it would be utilized in service. With particular reference to FIG. 1, the device 10 is used to detect and indicate the presence of corrosive fluids, in a volume V defined by one or more walls 12. The volume V may be a chamber or it may be a conduit. The volume V may also be the interior of an insulating jacket defined by a wall 12 of insulation wrapped around a pipe (not shown) in a heavy water plant. In any event the volume V is not normally subject to corrosive fluids but should a corrosive fluid leak thereinto or be formed therein it is desirable and necessary to be aware of the presence of such fluids as soon as possible so that corrective measures may be taken.

The device 10 includes a generally cylindrical body or housing 14 which is receivable in an opening 16 in the wall section 12. The opening 16 should be chamfered or cut away as at 18 to better expose the end wall 20 of the housing 14 to the volume V. The housing 14 has a central bore 22 terminating at the end wall 20. A central opening 24 in the end wall 20 serves to communicate the central bore 22 with the volume V, although further communication may be achieved with side slots 26. Slots 26 would be exposed to the volume V by the cut-away portion 18 of the opening 16.

Housing 14 has a plurality of circumferential or peripheral grooves 28 in the outer surface thereof. The grooves are axially positioned to correspond to different wall thicknesses such as ⅝, ⅞ and 1⅜ inches. An annular push-on flange 30 has a central opening corresponding to the innermost circumference of the grooves 28 and a plurality of radial slits 32 extending outwardly from the opening. The flange 30 may be pushed onto the housing 14 due to the flexibility of the portions between the slits 32 until the inner periphery thereof resides in the appropriate groove 28. The device may be inserted in the opening 16 until the flange 30 abuts the outer surface of the wall 12. The flange is then sealed and secured to the wall 12 as by welding, an adhesive, or any other suitable means.

Positioned within the bore 22 so as to be slidably received therein is a bobbin 34 having circular end walls or flanges 36,38 and a central joining shaft 40. A bright coloured ribbon 42 is affixed at one end to the shaft 40 and is then wrapped tightly on the shaft 40 to occupy the annular space between the end flanges 36,38. Ribbon 42 will be long, perhaps as long as 5 or 6 feet and the combination of its length and bright colour will make it highly visible. The ribbon, and the bobbin to which it is attached, make up the primary indicator of the present invention.

A secondary indicator 44 is also provided in the bore 22, indicator 44 having a head portion 46 and a shaft portion 48. The head portion 46 has a sliding fit in bore 22 and the shaft portion is of a lesser diameter and extends axially from the head portion to abut with the primary indicator. To facilitate the abutment, the shaft portion 48 has a conical tip 50, the apex of which is receivable in a corresponding countersunk bore 52 axially provided in the end flange 38 of bobbin 34. A string or other connector 54 is attached at one end to the shaft portion 48 and at the other end to the free end of the ribbon 42. A slot in the end flange 38 permits the string 54 to pass unobstructedly from the shaft portion to the free end of the ribbon 42.

A compression spring 56 is contained within the bore 22 so as to be contained between the end wall 20 and the head portion 46 of the secondary indicator. A cup-shaped, circular spring retainer 58 having a peripheral flange 60 is positioned between the spring and the head portion 46. Spring retainer 58 also has an axial through bore, through which passes a corrodable link 64. Link 64 is selected from the group of materials known to be affected by the particular corrosive fluid to be detected. For example a link formed of low carbon steel or perhaps of commerical copper would be suitable for detecting the acids formed from H₂S, water and oxygen.

The link 64 has an enlarged end preventing its complete passage through bore 62 and the other end is affixed to a retainer bar 66 which extends across opening 24 in end wall 20 and is supported by the end wall 20. Recesses may be provided in end wall 20 to positively locate the retainer bar 66.

With the corrodable line 64 in place the compression spring 56 will be held in a state of compression thereby and both the primary and the secondary indicators will be completely positionable in the bore 22. A weather seal 68 formed of a material such as sealing wax may then be placed over the open end of bore 22 to protect the elements in the bore from any contamination that could affect its performance.

Finally a retaining pin 70 is provided in the bore 22, anchored at each end in the wall of the housing 14. Pin 70 is located adjacent shaft portion 48 and serves to limit, by abutment with head portion 46, the extent that the secondary indicator 44 may move outwardly in the bore 22.

The materials for the various elements should be selected so that there will be no deterioration thereof in the corrosive fluid to which the device will be exposed, the exception of course being the link 64. The bobbin 34, ribbon 42, indicator 44, flange 30 and housing 14 may be satisfactorily formed from a plastics material such as polytetrafluorethylene, while the spring 56, pin 70 and bar 66 may be formed from stainless steel.

In use, the device of the present invention is purchased in the assembled form of FIGS. 1 and 3 with the link 64 holding the spring 56 in compression and with the primary and secondary indicators sealed within the bore 22 by the seal member 68. The flange 30 is positioned in the appropriate groove 28, depending on the wall thickness, the device is inserted in the opening 16 and the flange is sealingly secured to the outer surface of the wall 12.

Should the volume V be subjected to a corrosive fluid, the fluid will eventually contact one or more of the devices 10 and the link 64 will be exposed to the corrosive fluid via opening 24 and slots 26. The fluid will act on the link, corroding it until it has weakened sufficiently that the axial force imposed thereon by the spring 56 will be enough to fracture and completely sever the link. Since the link was the only element holding the spring 56 in compression, the spring force following severance of the link 64 will act on the secondary indicator to act on the primary indicator to fracture the seal 68 and to almost explosively eject the primary indicator from the bore 22 (see FIG. 2). The ribbon 42, attached as it is to the shaft portion 48 will unroll from the bobbin 34 to provide a long, bright streamer connected to the device 10 thereby providing a visual signal that corrosive fluid has been detected. The secondary indicator is prevented from exiting the bore 22 due to the limiting action of the retainer pin 70 acting on the head portion 46. However the tip of the shaft portion 48 will project slightly from bore 22 and it may also be brightly coloured to act as a visual backup to the ribbon 42. It would also be possible, although not specifically illustrated herein, to provide the device of the present invention with electrical contacts which could be closed upon abutment of the head portion 46 with the retaining pin 70 to activate an audible alarm. If the activated device were one of a series of such devices provided in a specific area, the audible alarm would alert the operator to a problem in that area and the ribbon 42 would visually identify the exact detector which had been activated.

The present invention has been described primarily with respect to an environment which produces an acidic fluid which in turn will corrode the link 64 to activate the primary and secondary indicators thereof. It is contemplated that the invention could be utilized in other types of potentially hostile environments wherein the link is subject to chemical attack for example, and hence the words "corrode", "corrosion", et cetera are intended to apply equally to such situations, wherein the material of the link is selected so that it will be severed, or even become unbonded, upon attack by the hostile environment it is intended to react to.

Also, it is not essential to provide a secondary indicating means per se as the spring 56 could act directly on the bobbin 34 while the link is retained by the retaining means 58 and 66. This structure would represent a simplified, and the most basic, version of the invention. Suitable means, such as an inwardly directed flange, or an internal circlip, could be provided in the bore 22 to prevent the spring 56 and retainer 58 from exiting the bore when the link 64 is severed through reaction with the hostile environment. In this instance the spring 54 would be connected to the housing rather than to a secondary indicator.

The aforegoing disclosure is intended to describe the best method of constructing and utilizing the present invention. It is understood that skilled practitioners in the art could modify the structure of the present invention without departing from the spirit thereof. Accordingly the scope of protection to be afforded the present invention should be determined from the appended claims.

The embodiments of the invention in which an exclusive property or privilege is claimed are defined as follows:

1. A device for detecting and indicating the presence of a corrosive fluid in a volume substantially at atmospheric pressure, comprising:
   a hollow housing having open inner and outer ends;

primary indicating means movably mounted in said housing between a stored position in said housing and an indicating position outside of said housing;

compression spring means, in said housing adjacent and coupled to said primary indicating means, for projecting said primary indicating means from said housing to said indicating position; and corrodable link means for holding said spring means in compression and said primary indicating means in said stored position;

whereby, when said link means is severed through corrosion thereof, said spring means forcibly projects said primary indicating means to said indicating position outside of said housing.

2. The device of claim 1 wherein said housing has an end wall having an opening therethrough, and a central bore therein containing said spring means and, prior to activation of said device, said primary indicating means.

3. The device of claim 2 wherein said primary indicating means includes a bobbin slidable receivable in said bore and a ribbon wrrapped on said bobbin, one end of said ribbon being retained with said housing.

4. The device of claim 3 wherein said link means is connected at one end to a retainer positioned intermediate said spring means and said bobbin and at the other end to a retaining bar abutting an outer surface of said housing end wall, said link means passing through said opening therein.

5. The device of claim 1 and including secondary indicating means in said housing between said spring means and said primary indicating means, said spring means, in activation of said device, acting on said secondary indicating means to project said primary indicating means from said housing.

6. The device of claim 5 wherein, when said primary indicating means is projected to said indicating position, said secondary indicating means takes up an indicating position in said housing.

7. The device of claim 6 wherein said housing has an end wall having an opening therethrough, a central bore therein containing said spring means, said secondary indicating means and, prior to activation of said device, said primary indicating means.

8. The device of claim 7 wherein said primary indicating means includes a bobbin slidably receivable in said bore and a ribbon wrapped on said bobbin, and wherein said secondary indicating means includes a head portion adjacent said spring means with a sliding fit in said bore and a shaft portion in abutment with said bobbin, said shaft portion being connected to one end of said ribbon.

9. The device of claim 8 wherein said link means is connected at one end to a retainer positioned intermediate said spring means and said head portion and at the other end to a retaining bar abutting an outer surface of said housing end wall, said link passing through said opening therein.

10. The device of claim 9 and including means to limit travel of said secondary indicating means within said bore.

11. A device for detecting and indicating the presence of a corrosive fluid in a volume defined by one or more wall sections, comprising:

an indicator body sealing receivable in an opening in one of the wall sections, said body having a bore therein terminating at an end wall and an opening in said end wall providing fluid communication between said bore and the volume;

a primary indicator movably mounted in said bore between a primary stored position in said body and a primary indicating position outside of said body;

a secondary indicator movably mounted in said bore between a secondary stored position and a secondary indicating position and abutting said primary indicator in said stored positions;

means connecting said primary indicator to said secondary indicator;

seal means extending across and closing an end of said bore opposite said opening in said end wall;

compression spring means, in said bore between said secondary indicator and said end wall, for projecting said primary indicator through said seal means and from said housing to said primary indicating position and for moving said secondary indicator to said second indicating position; and a corrodable link normally connecting said secondary indicator with said end wall to hold said spring means in compression and to hold said primary and secondary indicators in said stored positions, said link being severable under corrosive action of the fluid;

whereby, when said link is severed by corrosive fluid in the volume, said spring means will exert a force on said primary and secondary indicators to break said seal means and to thereafter project said primary indicator to said primary indicating position outside said body to indicate the presence of corrosive fluid in the volume.

12. The device of claim 11 wherein said primary indicator includes a bobbin slidably receivable in said bore and a ribbon connected at one end to said bobbin and wrapped therearound, said connecting means connecting said secondary indicator to the other end of said ribbon.

13. The device of claim 12 wherein said secondary indicator includes a head portion having a sliding fit in said bore and a shaft portion of lesser diameter extending axially therefrom for abutting engagement with said bobbin.

14. The device of claim 11, 12, or 13 wherein said link is connected at one end to a retaining bar which abuts against an outer surface of said end wall, and at the other end to a spring retainer abutting said secondary indicator, said link extending through said opening in said end wall and along the axis of said spring means.

15. The device of claim 13 and including a retaining pin in said bore for limiting the distance said secondary indicator may move in said bore following severance of said link.

16. The device of claim 11, wherein said body has a plurality of peripheral grooves in the outer surface thereof and a push-on flange having an adjustable opening therein for receiving said body, said flange engaging a selected one of said grooves about the opening therein.

17. An indicator for indicating the presence of corrosive fluids in a volume defined by a plurality of wall sections, comprising:

an indicator body sealingly receivable in an opening in one of the wall sections, said body being cylindrical, having a central bore extending from one end thereof and terminating at an end wall at the other end thereof and having an opening in said wall providing fluid communication between said bore and the volume;

a primary indicator movable between a stored position in said body and an indicating position outside of said body and including a bobbin and a ribbon connected at one end to and wrapped on said bobbin, said bobbin and ribbon being slidably received in said bore;

a secondary indicator contained in said bore inwardly of said bobbin and in contact therewith, said secondary indicator having a head portion having a sliding fit with said bore and a shaft portion contacting said bobbin;

means connecting said shaft portion of said secondary indicator with the other end of said ribbon;

a compression spring positioned in said bore between said end wall and said head portion;

a corrodable link connected between said head portion and said end wall for exposure to the volume, said link holding said spring in compression, said link being severable under corrosive action of the fluid;

seal means normally sealing said one end of said bore; and a retaining pin in said bore for abutment with said head portion to prevent said secondary indicator from exiting from said bore upon release of said spring;

whereby, upon severance of said link under said corrosive action, said spring will exert a force on said secondary indicator to act in turn on said bobbin to break said seal means and to thereafter project said bobbin from said bore to said indicating position so that said ribbon will unwind from said bobbin to provide a visual indication of the presence of corrosive fluids.

* * * * *

UNITED STATES PATENT AND TRADEMARK OFFICE
CERTIFICATE OF CORRECTION

PATENT NO. : 4,271,120

DATED : June 2, 1981

INVENTOR(S) : Louis Marc Michaud

It is certified that error appears in the above-identified patent and that said Letters Patent are hereby corrected as shown below:

In column 5, line 63, "sealing" should read --sealingly--.

Signed and Sealed this

Twenty-fifth Day of August 1981

[SEAL]

Attest:

Attesting Officer

GERALD J. MOSSINGHOFF

Commissioner of Patents and Trademarks